United States Patent [19]

Maurer et al.

[11] Patent Number: 4,659,846

[45] Date of Patent: Apr. 21, 1987

[54] PREPARATION OF 2,5-DILOWERALKYL-1.4:3,6-DIANHYDROSORBITOLS

[75] Inventors: Manfred Maurer, Kirchheim/Weinstrasse; Winfried Orth, Hassloch/Pfalz; Werner Fickert, Mannheim, all of Fed. Rep. of Germany

[73] Assignee: Rutgerswerke Aktiengesellschaft, Fed. Rep. of Germany

[21] Appl. No.: 859,006

[22] Filed: May 2, 1986

[30] Foreign Application Priority Data

Jun. 19, 1985 [DE] Fed. Rep. of Germany ....... 3521809

[51] Int. Cl.$^4$ ............................................. C07D 493/04
[52] U.S. Cl. .................................................... 549/464
[58] Field of Search ........................................... 549/464

[56] References Cited

U.S. PATENT DOCUMENTS

| 2,420,519 | 5/1947 | Brown | 549/464 |
| 4,322,359 | 3/1982 | Hillard et al. | 549/464 |
| 4,435,586 | 3/1984 | Kruse et al. | 549/464 |

*Primary Examiner*—Henry R. Jiles
*Assistant Examiner*—Bernard I. Dentz
*Attorney, Agent, or Firm*—Bierman & Muserlian

[57] ABSTRACT

In a process for the preparation of 2,5-diloweralkyl-1,4; 3,6-dianhydrosorbitols by reacting 1,4;3,6-dianhydrosorbitol with an alkylating agent in an alkaline aqueous-organic solvent solution, the improvement comprising using a tertiary alkanol as the organic solvent.

7 Claims, No Drawings

PREPARATION OF 2,5-DILOWERALKYL-1.4:3,6-DIANHYDROSORBITOLS

STATE OF THE ART 2,5-dialkyl-1,4; 3,6-dianhydrosorbitols are known to possess exceptional compatability with water and organic solvents and 2,5-dimethyl-1,4; 3,6-dianhydrosorbitol or dimethyl isosorbide is a widely used solvent in pharmaceutical and cosmetics compositions. U.S. Pat. No. 4,322,359 describes the preparation of isosorbide by dissolving 1,4; 3,6-dianhydrosorbitol in a mixture of an alkaline aqueous medium and a water-miscible solvent free of hydroxyl groups and then methylating the same with dimethyl sulfate. The final product is recovered by extraction and is purified by distillation to obtain an 82.6% yield of dimethyl isosorbide which is not a satisfactory yield for valuable products.

OBJECTS OF THE INVENTION

It is an object of the invention to provide an economical process for the preparation of 2,5-diloweralkyl-1,4; 3,6-dianhydrosorbitols in high yields.

This and other objects and advantages of the invention will become obvious from the following detailed description.

THE INVENTION

The novel process of the invention for the preparation of 2,5-dialkyl-1,4; 3,6-dianhydrosorbitols with alkyls of 1 to 5 carbon atoms comprises reacting 1,4;3,6-dianhydrosorbitol with an alkylating agent in solution in an alkaline water-tertiary alkanol mixture. The use of the tertiary alkanol surprisingly results in a trouble-free reaction with high yields of the desired dialkylated products. This was surprising in view of the teaching of U.S. Pat. No. 4,322,359 that the selection of the organic cosolvent was critical for the reaction and that hydroxylated solvents results in low yields, if any, of dimethyl isosorbide due to side reactions.

Examples of suitable alkylating agents are those known to the art such as methyl iodide, dimethylsulfate, diethylsulfate and p-toluene sulfonic acid esters. Examples of suitable tertiary alkanols are those of 4 to 8 carbon atoms such as tert.-butanol and tert.-amyl alcohol.

In a preferred mode of the process, 1,4; 3,6-dianhydrosorbitol is dissolved in 2 to 4 times its amount in a tertiary alkanol such as tert.-butanol with heating to 40° to 70° C. and the aqueous alkaline solution and the alkylating agent are simulanteously added thereto in a manner so that the mixture always has an alkaline pH.

Examples of suitable alkaline aqueous solutions are solutions of bases such as alkali metal and alkaline earth metal carbonates and hydroxides. Preferred are aqueous solutions of 40 to 60% by weight of sodium hydroxide or potassium hydroxide.

The start of the reaction is exothermic and the reaction will usually take place at reflux and in the case of a low-boiling alkylating agent, under pressure. External cooling may be used to maintain the reaction temperature between 50° and 120° C., if desired. After the reaction is complete, i.e. 2 to 15 hours, the tert.-alkanol is removed by distillation and the residue is dissolved in water and extracted with a water insoluble organic solvent such as methylene chloride, ethylene chloride, ether, trichloromethane, trichloroethane or toluene. The organic phase is then dried and evaporated to dryness and subjected to vacuum distillation to recover the desired product. The tertiary alkanol can be recycled after removal of water.

Due to the expense of 1,4; 3,6-dianhydrosorbitol, less expensive sorbitol is preferred as the starting material after removal of water by known means.

In the following examples there are described several preferred embodiments to illustrate the invention. However, it should be understood that the invention is not intended to be limited to the specific embodiments.

EXAMPLE 1

292.3 g (2 mol) of 1,4; 3,6-dianhydrosorbitol and 800 ml of tert.-butanol were heated to 55° to 65° C. with stirring and then two separate dropping funnels were used to simultaneously add 572 g (7.14 mol) of aqueous 50% sodium hydroxide solution and 631 g (5 mol) of dimethyl sulfate dropwise at this temperature while keeping the reaction mixture always alkaline. The mixture was then stirred for three hours at about 60° C. and then most of the tert.-butanol was distilled off. The residue was mixed with 2,600 ml of water and the resulting solution was extracted three times with 500 ml portions of methylene chloride. The combined organic phases were dried over potassium carbonate and evaporated first at atmospheric pressure and then distilled under water jet vacuum to obtain 324 g (93% yield) of dimethyl isosorbide with a boiling point of 118° to 120° C. at 20 mbar.

EXAMPLE 2

292.3 g (2 mol) of 1,4; 3,6-dianhydrosorbitol and 800 ml of tert.-butanol were heated to 70° to 80° C. with stirring and then two separate dropping funnels were used to add 572 g of (7.14 mol) of a 50% aqueous solution of sodium hydroxide and 770 g (5 mol) of diethyl sulfate dropwise at this temperature while keeping the reaction mixture always alkaline. The mixture was stirred for three hours at 70° to 80° C. and then most of the tert.-butanol was distilled off. The residue was mixed with 2,600 ml of water and the resulting solution was extracted 3 times with 500 ml portions of toluene. The combined organic phases were dried over potassium carbonate and the solvent was evaporated off. The residue was distilled under water jet vacuum to obtain 368 g (91% yield) of diethyl isosorbide with a boiling point of 134° to 137° C. at 20 mbar.

EXAMPLE 3

Using the procedure of Example 1, 1,4; 3,6-dianhydrosorbitol was dissolved in tert.-amyl alcohol and 800 g (7.14 mol) of aqueous 50% potassium hydroxide were added. The extraction was effected with trichloromethane to obtain 318 g (92% yield) of dimethyl isosorbide.

EXAMPLE 4

292.3 g (2 mol) of 1,4; 3,6-dianhydrosorbitol and 800 ml of tert.-butanol were heated to 50° C. with stirring and then two separate dropping funnels were used to add 710 g (5 mol) of methyl iodide and 572 g (7.14 mol) of an aqueous 50% solution of sodium hydroxide dropwise while keeping the reaction mixture always alkaline. The mixture was stirred for 12 hours, during which time the pot temperature was increased to 80° C. and then the alcohol was removed by distillation 1,500 ml of water were added to the residue and the solution was extracted three times with 500 ml portions of ether. The combined organic phases were dried over potassium carbonate and the solvent was evaporated and the residue was distilled under water jet vacuum to obtain 314 g (91% yield) of dimethyl isosorbide with a boiling point of 118° to 126° C. at 20 mbar.

EXAMPLE 5

Using the procedure of Example 1, 930 g (5 moles) of methyl p-toluene sulfonate were reacted to obtain 315 g (91% yield) of dimethyl isosorbide.

EXAMPLE 6

1.548 g (8.5 mol) of sorbitol, 3,000 ml of xylene and 20 ml of concentrated sulfuric acid were heated to reflux with stirring and about 306 ml of water were removed. The xylene was then removed by distillation (the last amount under vacuum) and the residue was taken up in 3,000 ml of tert.-butanol, heated to 55° to 65° C., 2,432 ml (30.4 mol) of an aqueous solution of sodium hydroxide and 2,682 g (21.25 mol) of dimethyl sulfate were added dropwise simultaneously at this temperature while keeping the mixture always alkaline. When the addition is completed, the mixture was stirred for three hours at 60° C. and the alcohol was then removed up to a distillation temperature of 97° to 98° C. The residue was taken up in 8,500 ml of water and the aqueous solution was extracted three times with 1,000 ml portions of ethylene chloride. The solvent was evaporated from the combined organic phases and was fractioned in a column to recover the fraction in the boiling range of 118° to 120° C. mbar which was 1,037 g (70% yield) of dimthyl isosorbide.

Various modifications of the process may be made without departing from the spirit or scope thereof and it is to be understood that the invention is intended to be limited only as defined in the appended claims.

What we claim is:

1. In a process for the preparation of 2,5-diloweralkyl-1,4; 3,6-dianhydrosorbitols by reacting 1,4; 3,6-dianhydrosorbitol with an alkylating agent in an alkaline aqueous-organic solvent solution, the improvement comprising using a tertiary alkanol as the organic solvent.

2. The process of claim 1 wherein the tertiary alkanol is tert.-butanol.

3. The process of claim 1 wherein the tertiary alkanol is tert.-amyl alcohol.

4. The process of claim 1 wherein the aqueous alkaline solution is an aqueous solution of an alkali metal hydroxide.

5. The process of claim 4 wherein the alkali metal hydroxide is sodium hydroxide.

6. The process of claim 4 wherein the alkali metal hydroxide is potassium hydroxide.

7. The process of claim 1 wherein 1,4; 3,6-dianhydrosorbitol is obtained by removing water from sorbitol.

* * * * *